United States Patent
Hill et al.

(10) Patent No.: US 8,048,946 B2
(45) Date of Patent: *Nov. 1, 2011

(54) HYDROLYTICALLY STABLE PHOSPHITE COMPOSITIONS

(75) Inventors: Jonathan S. Hill, Manchester (GB); Maurice Power, Manchester (GB)

(73) Assignee: Chemtura Corporation, Middlebury, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 12/804,793

(22) Filed: Jul. 28, 2010

(65) Prior Publication Data

US 2011/0028619 A1   Feb. 3, 2011

Related U.S. Application Data

(60) Provisional application No. 61/230,654, filed on Jul. 31, 2009.

(51) Int. Cl.
*C08K 5/524* (2006.01)

(52) U.S. Cl. .......... 524/147; 252/400.23; 252/401; 524/151; 524/152; 524/153; 524/247; 524/249

(58) Field of Classification Search .......... 252/400.23, 252/401; 524/147, 151–153, 247, 249
See application file for complete search history.

(56) References Cited

U.S. PATENT DOCUMENTS

| | | | |
|---|---|---|---|
| 3,787,537 A | 1/1974 | DeMarcq | |
| 5,063,264 A * | 11/1991 | Nakajima | 524/118 |
| 5,561,181 A | 10/1996 | Mahood | |
| 7,375,149 B2 * | 5/2008 | Rotzinger et al. | 524/110 |
| 2008/0194743 A1 * | 8/2008 | Rotzinger et al. | 524/111 |
| 2009/0326112 A1 * | 12/2009 | Gelbin et al. | 524/132 |
| 2010/0025636 A1 * | 2/2010 | Gelbin et al. | 252/400.24 |
| 2010/0069542 A1 * | 3/2010 | Gelbin et al. | 524/147 |
| 2010/0076125 A1 * | 3/2010 | Gelbin et al. | 524/100 |
| 2010/0076131 A1 * | 3/2010 | Gelbin et al. | 524/130 |
| 2010/0190900 A1 * | 7/2010 | Gelbin et al. | 524/132 |
| 2010/0197837 A1 * | 8/2010 | Zahalka et al. | 524/101 |
| 2011/0024677 A1 * | 2/2011 | Hill et al. | 252/182.3 |
| 2011/0028616 A1 * | 2/2011 | Gelbin et al. | 524/151 |
| 2011/0028617 A1 * | 2/2011 | Hill et al. | 524/151 |
| 2011/0028618 A1 * | 2/2011 | Gelbin et al. | 524/153 |

FOREIGN PATENT DOCUMENTS

| | | |
|---|---|---|
| EP | 0 143 464 A2 | 6/1985 |
| EP | 0 167 969 A2 | 7/1985 |
| WO | WO 2007/009916 A1 | 1/2007 |
| WO | WO 2007149143 A2 | 12/2007 |

OTHER PUBLICATIONS

Chemtura Weston® 399 Technical information paper, XP-002619353.
Plastics Additives Handbook—6$^{th}$ edition—Hans Zweifel et al, Hanser Publishers, (Munich 2000) pp. 109-112.

* cited by examiner

*Primary Examiner* — Peter Szekely
(74) *Attorney, Agent, or Firm* — Joseph Suhadolnik

(57) ABSTRACT

Hydrolytically stable phosphites as secondary antioxidants for polymer resins comprising a phosphite and an amine compound. The phosphite may be a liquid phosphite composition. The amine compound may have the structure of formula I:

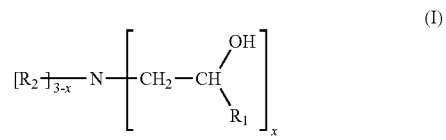

wherein x is 1, 2 or 3; $R_1$ is selected from the group consisting of hydrogen, and straight or branched $C_1$-$C_6$ alkyl, and $R_2$ is selected from the group consisting of straight or branched $C_1$-$C_{30}$ alkyl.

8 Claims, No Drawings

HYDROLYTICALLY STABLE PHOSPHITE COMPOSITIONS

This application claims benefit under 35 USC 119(e) of U.S. provisional application No. 61/230,654, filed Jul. 31, 2009, the disclosure of which is incorporated by reference.

FIELD OF THE INVENTION

The present invention relates to a novel composition of phosphite antioxidants that are hydrolytically stabilized with an amine. It also relates to stabilized polymers and stabilizer concentrates comprising the novel hydrolytically stable liquid composition of phosphite antioxidants.

BACKGROUND OF THE INVENTION

Organic phosphites are known in the art as secondary antioxidants for polymeric resins such as polyolefins and elastomers. As an antioxidant, these phosphites are oxidized to phosphates to prevent oxidation of the polymer. Examples of such phosphites are disclosed in H. Zweifel (Ed) *Plastics Additives Handbook*, 5th edition, Hanser Publishers, Munich 2000. One common problem for most phosphites is the tendency to undergo unfavorable hydrolysis upon exposure to moisture or water, even trace amounts, during storage or handling. Initially, hydrolysis of the phosphite generates acidic P—OH and PH=O protons that are good reducing agents that react directly with oxygen or hydroperoxides. However, if hydrolysis continues past this initial stage, stronger acids are formed that greatly accelerate the formation of oxidized products. Additionally, other acids from impurities arising from residues of polymerization catalysts may further catalyze the phosphite hydrolysis. These oxidized products lessen the overall ability of the phosphite stabilizer to function as an antioxidant. As a result of exposure to water, hydrolyzed phosphites become a lumpy, sticky mass that leads to corrosion of processing equipment.

Conventionally, to prevent hydrolysis, producers have sought phosphites that are slow to hydrolyze and have added various hydrolysis stabilizers to the phosphites. U.S. Pat. No. 3,787,537 describes a triisopropyl phenyl phosphite ester that is slow to hydrolyze in combination with a heavy amine to further increase the stability to hydrolysis.

Trialkylaryl phosphite stabilizers having hindered alkyl groups at the ortho and para positions are resistant to hydrolysis due to steric hindrance. One of the most widely used phosphites is tris(2,4-di-t-butylphenyl)phosphite, which is commercially sold under the trade name Alkanox™ 240, Irgafos™ 168 or Doverphos™ S-480. This phosphite is a solid and is commercially available without a hydrolysis stabilizer.

Other trialkylaryl phosphite stabilizers, such as the widely used tris(p-nonylphenyl) phosphite (TNPP) are susceptible to hydrolysis. TNPP is a liquid at room temperature. Commercial grades of TNPP, such as Weston™ 399 (Chemtura Corporation), usually contain up to 1 wt % of triethanolamine or triisopropanolamine, which acts as an hydrolysis stabilizer.

U.S. Pat. No. 5,561,181 discloses a highly ortho-substituted TNPP that is more hydrolytically stable than para-substituted TNPP.

EP0167969 discloses a phosphite that is hydrolytically stabilized with a long-chain aliphatic amine, such as coconutalkyl diethanolamine. EP0143464 discloses a pentaerythritol diphosphite that is hydrolytically stabilized with a long-chain aliphatic amine, such as octyldecyl diethanolamine.

There is, however, a need to replace TNPP owing to alleged estrogenicity concerns associated with nonylphenol, which is used in synthesizing TNPP.

Thus, the need exists for safe and effective liquid phosphite compositions for use as secondary antioxidants in polymers that may be hydrolytically stabilized.

In addition, there is a need for amine compounds that are suitable for the hydrolytic stabilization of a wider range of phosphite antioxidants.

SUMMARY OF THE INVENTION

In a first aspect, the invention is directed to a composition comprising: (a) a phosphite, preferably a liquid phosphite composition and (b) an amine having the structure:

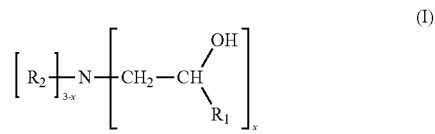

wherein x is 1, 2 or 3; $R_1$ is selected from the group consisting of hydrogen, and straight or branched $C_1$-$C_6$ alkyl, and $R_2$ is selected from the group consisting of straight or branched $C_1$-$C_{30}$ alkyl. Preferably, x is 1 or 2. The amine may be present in an amount from 0.01 to 3 wt %, based on the total weight of the composition. The liquid phosphite composition comprises at least two different phosphites of the following: (i) a tris(dialkylaryl)phosphite, (ii) a tris(monoalkylaryl)phosphite, (iii) a bis(dialkylaryl)monoalkylaryl phosphite, and (iv) a bis(monoalkylaryl)dialkylaryl phosphite; wherein and is a liquid at ambient conditions.

In a second aspect, the present invention is directed to composition comprising: (a) a liquid phosphite composition and (b) a bis(2-alkanol)mono-$C_8$-$C_{20}$-alkyl amine. The liquid phosphite composition comprises at least two different phosphites of the following: (i) a tris(dialkylaryl)phosphite, (ii) a tris(monoalkylaryl)phosphite, (iii) a bis(dialkylaryl) monoalkylaryl phosphite, and (iv) a bis(monoalkylaryl)dialkylaryl phosphite; and is a liquid at ambient conditions.

In a third aspect, the present invention is directed to a process for hydrolytically stabilizing a secondary antioxidant comprising adding to the secondary antioxidant an amine in the amount of from 0.01 to 3 wt %. The amine has the structure

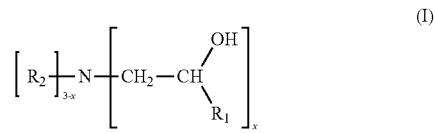

wherein x is 1, 2 or 3; $R_1$ is selected from the group consisting of hydrogen, and straight or branched $C_1$-$C_6$ alkyl, and $R_2$ is selected from the group consisting of straight or branched $C_1$-$C_{30}$ alkyl. Preferably, x is 1 or 2. The liquid phosphite composition comprises at least two different phosphites of the following: (i) a tris(dialkylaryl)phosphite, (ii) a tris (monoalkylaryl)phosphite, (iii) a bis(dialkylaryl)monoalkylaryl phosphite, and (iv) a bis(monoalkylaryl)dialkylaryl phosphite; and is a liquid at ambient conditions.

DETAILED DESCRIPTION OF THE INVENTION

The present invention relates to stabilized phosphite compositions comprising one or more phosphite compounds and one or more amine compounds that are capable of hydrolytically stabilizing the phosphite compound. The phosphite compounds according to the present invention are stabilized with one or more amines, e.g., one or more alkanolamines, preferably one or more alkan-2-olamines, i.e., wherein the hydroxyl group or groups are on a beta carbon. The amine compound may have a primary, secondary, or tertiary nitrogen. In one embodiment, the nitrogen atom is substituted with at least one alkanol group and optionally one or more alkyl groups, which preferably facilitate dispersing or solubilizing the amine compound into the phosphite compound or mixture of phosphite compounds.

Phosphites and phosphonites are well known and include, for example, triphenyl phosphites, diphenylalkyl phosphites, phenyldialkyl phosphites, tris(nonyl-phenyl)phosphites, trilauryl phosphites, trioctadecyl phosphites, distearyl pentaerythritol diphosphites, tris(2,4-di-tert-butylphenyl)phosphites, diisodecyl pentaerythritol diphosphites, bis(2,4-di-tert-butylphenyl)pentaerythritol diphosphites tristearyl sorbitol triphosphites, bis(2,4-dicumylphenyl)pentaerythritol diphosphites, and tetrakis(2,4-di-tert-butylphenyl)4,4'-biphenylene diphosphonites; specific phosphite compounds include, for example, triphenyl phosphite, tris(nonyl-phenyl) phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, tristearyl sorbitol triphosphite, tris(dipropyleneglycol)phosphite, and tetrakis(2,4-di-tert-butylphenyl)4,4'-biphenylene diphosphonite. Preferably, the phosphite is a liquid phosphite composition.

In one embodiment, the phosphite is a liquid tris(mono-alkyl)phenyl phosphite ester or a liquid mixture of liquid tris(mono-alkyl)phenyl phosphite esters, as described in U.S. Pat. No. 7,468,410, the entire contents and disclosures of which are hereby incorporated by reference. For example, the phosphite is a tris(monoalkylphenyl)phosphite or a liquid mixture of two or more tris(monoalkylphenyl)phosphites, for example, tris(monoalkylphenyl)phosphites wherein the alkyl substituent is a straight or branched chain alkyl of 1 to 20 carbon atoms, for example 1 to 8 carbon atoms. In one particular embodiment, the phosphite contains one or more of tris(3-t-butylphenyl)phosphite, tris(2-sec-butylphenyl)phosphite, or tris(4-sec-butylphenyl)phosphite. In one embodiment, the liquid mixture comprises different phosphites, one of which is tris(3-t-butylphenyl)phosphite, tris(2-sec-butylphenyl)phosphite, or tris(4-sec-butylphenyl)phosphite and the other of which is tris(3-t-butylphenyl)phosphite, tris(2-sec-butylphenyl)phosphite, tris(4-sec-butylphenyl)phosphite, tris(2-t-butylphenyl)phosphite, tris(4-t-butylphenyl)phosphite, or tris(2,4-di-t-butylphenyl)phosphite.

Amine Stabilizers

In one aspect, the amine stabilizer has the structure of formula I:

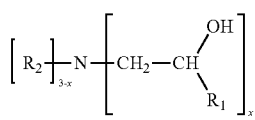

(I)

wherein x is 1, 2 or 3, preferably, x is 1 or 2; $R_1$ is selected from the group consisting of hydrogen, and straight or branched $C_1$-$C_6$ alkyl, and $R_2$ is selected from the group consisting of straight or branched $C_1$-$C_{30}$ alkyl. Preferably $R_1$ is selected from the group consisting of straight or branched $C_1$-$C_4$ alkyl, e.g., methyl or ethyl. Preferably $R_2$ is selected from the group consisting of straight or branched $C_5$-$C_{20}$ alkyl, e.g., straight or branched $C_{10}$-$C_{20}$ alkyl or straight or branched $C_{12}$-$C_{18}$ alkyl. In one embodiment, x is 1 and $R_2$ is straight or branched $C_5$-$C_{20}$ alkyl, e.g., $C_{12}$-$C_{18}$ alkyl. In one embodiment, x is 2 and $R_2$ is straight or branched $C_{10}$-$C_{20}$ alkyl, e.g., $C_{12}$-$C_{18}$ alkyl Thus, in a particularly preferred aspect, the amine has the structure of formula (II):

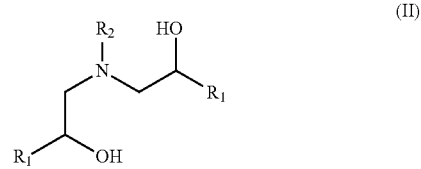

(II)

wherein $R_1$ is independently selected from the group consisting of hydrogen and straight or branched $C_1$-$C_6$ alkyl, preferably methyl, and $R_2$ comprises a straight or branched $C_8$-$C_{20}$ alkyl group, e.g., a straight or branched $C_{10}$-$C_{18}$ alkyl group or a straight or branched $C_{12}$-$C_{18}$ alkyl group.

In one embodiment, the amine comprises a bis(2-alkanol) mono-$C_8$-$C_{20}$-alkyl amine. The bis(2-alkanol)mono-$C_8$-$C_{20}$-alkyl amine, for example, is selected from the group consisting of octyl-bis(2-ethanol)amine, nonyl-bis(2-ethanol)amine, decyl-bis(2-ethanol)amine, undecyl-bis(2-ethanol)amine, dodecyl-bis(2-ethanol)amine, tridecyl-bis(2-ethanol)amine, tetradecyl-bis(2-ethanol)amine, pentadecyl-bis(2-ethanol)amine, hexadecyl-bis(2-ethanol)amine, heptadecyl-bis(2-ethanol)amine, octadecyl-bis(2-ethanol)amine, octyl-bis(2-propanol)amine, nonyl-bis(2-propanol)amine, decyl-bis(2-propanol)amine, undecyl-bis(2-propanol)amine, dodecyl-bis(2-propanol)amine, tridecyl-bis(2-propanol)amine, tetradecyl-bis(2-propanol)amine, pentadecyl-bis(2-propanol)amine, hexadecyl-bis(2-propanol)amine, heptadecyl-bis(2-propanol)amine, octadecyl-bis(2-propanol)amine, and isomers thereof. Suitable, commercially available amines include Armostat™ 300 and Armostat 1800.

In another aspect, the amine has the structure of formula (III):

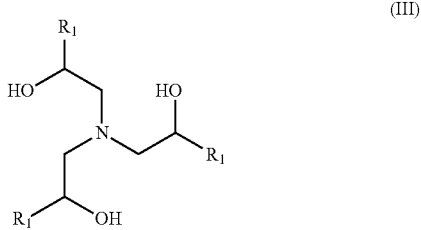

(III)

wherein each $R_1$ is independently selected from the group consisting of hydrogen, straight or branched $C_1$-$C_6$ alkyl. In preferred aspects, $R_1$ is a straight or branched $C_1$-$C_3$ alkyl group, preferably methyl.

Exemplary amine compounds of formula (III) include compounds selected from the group consisting of triethanolamine, triisopropanolamine (TIPA), tributanolamine, and tripentanolamine.

Other exemplary amines suitable for stabilizing phosphite composition include diethanolamine, diisopropanolamine, and tetraisopropanolethylenediamine.

The amount of stabilizer needed to effectively stabilize the phosphite composition may vary widely depending on the number of hydroxyl groups on each amine molecule, the compatibility, e.g., miscibility, of the amine with the phosphite composition, and the specific phosphite compounds included in the phosphite composition to be stabilized. In some exemplary embodiments, the stabilized phosphite composition comprises the one or more amines in an amount ranging from 0.01 to 3 wt. %, e.g., from 0.1 to 1.5 wt. %, or from 0.2 to 0.8 wt. %, based on the total weight of the stabilized phosphite composition. In one embodiment, the stabilized phosphite composition comprises 0.7 wt. % of the one or more amines.

It should be noted that certain phospites combined with certain alkanolamines generate a turbid mixture. For example tri-isopropanol amine is effective at hydrolytically stabilizing phosphites but will not always result in a clear mixture. On the other hand, as seen in the appended examples, octadecylbis (2-hydroxyethyl)amine will provide the same stability as tri-isopropanol but will generally do so without the generation of turbidity.

Liquid Phosphite Composition

While almost any phosphite may be found in the present phosphite composition, for example as discussed above, in various embodiments, the liquid phosphite composition, which is stabilized by the amine, comprises at least two different phosphites. Suitable liquid phosphite compositions are described, for example, in U.S. application Ser. No. 11/787,531, entitled LIQUID PHOSPHITE BLENDS AS STABILIZERS, the entire contents and disclosure of which are hereby incorporated by reference.

In some preferred embodiments, the phosphite composition comprises at least two different phosphites having the structure of formula V.

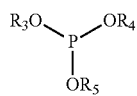

(V)

wherein $R_3$, $R_4$ and $R_5$ are independently selected alkylated aryl groups and wherein the liquid phosphite composition is a liquid at ambient conditions. By "ambient conditions" it is meant room temperature, e.g., 25° C., and 1 atmosphere pressure.

The aryl moiety of $R_3$, $R_4$ and $R_5$ is preferably an aromatic moiety of from 6 to 18 carbon atoms, e.g., phenyl, naphthyl, phenanthryl, anthracyl, biphenyl, terphenyl, o-cresyl, m-cresyl, p-cresyl, and the like, preferably phenyl. Each aromatic moiety is substituted with at least one $C_1$-$C_{18}$, e.g., $C_4$-$C_{10}$, or $C_4$-$C_5$ alkyl group. Preferably no aromatic moieties are substituted with any $C_9$ alkyl groups. The aromatic moieties may be mono-, di-, or tri-substituted in the ortho and/or para positions, but in many of these mixtures the phosphites themselves are not exclusively mono-substituted, are not exclusively di-substituted, and are not exclusively tri-substituted.

For example, the invention is to a stabilized liquid phosphite composition comprising a liquid phosphite composition and an amine compound, wherein the liquid phosphite composition comprises at least two of a tris(dialkylaryl)monophosphite, a tris(monoalkylaryl)phosphite, a bis(dialkylaryl) monoalkylaryl phosphite, and a bis(monoalkylaryl) dialkylaryl phosphite, wherein the phosphite composition is a liquid at ambient conditions. Thus, the liquid phosphite composition comprises at least one phosphite that has at least one aromatic moiety that is multiply substituted, such as a bis (dialkylaryl)monoalkylaryl phosphite, a bis(monoalkylaryl) dialkylaryl phosphite, or a tris(dialkylaryl)phosphite. The liquid phosphite composition also preferably includes at least one phosphite compound in which each aryl moiety is entirely monosubstituted, e.g., a tris(monoalkylaryl)phosphite. The alkyl group in the alkylaryl phosphite compounds preferably comprises a $C_3$-$C_5$ alkyl group, e.g., a $C_4$-$C_5$ alkyl group, most preferably t-butyl and/or t-amyl, and the aryl group preferably comprises phenyl or cresyl, e.g., o-, m-, and/or p-cresyl.

More generally, the alkyl substituent(s) on the aryl moieties of formula (V) are selected from straight-chain or branched $C_1$-$C_{18}$ alkyl, e.g., $C_1$-$C_8$ alkyl, $C_4$-$C_6$ alkyl, or $C_4$-$C_5$ alkyl, preferably $C_4$ alkyl or $C_5$ alkyl. In a preferred embodiment, the alkyl substituent(s) is not $C_8$-$C_{10}$ alkyl, e.g., not $C_9$ alkyl. The alkyl substituent may include, for example, methyl, ethyl, propyl, butyl, amyl, hexyl, heptyl, octyl, nonyl (although less preferred), decyl, undecyl, dodecyl, tridecyl, tetradecyl, pentadecyl, hexadecyl, heptadecyl, octadecyl, and isomers thereof. Most preferably, the alkyl group(s) are selected from butyl (especially sec-butyl and/or tert-butyl), and amyl groups (especially sec-amyl, tert-amyl, and/or iso-amyl). As indicated above, in one embodiment, the alkyl moieties do not include nonyl, meaning the phosphite composition preferably comprises less than 50 wppm, e.g., less than 10 wppm, or less than 5 wppm, nonyl substituted aryl phosphite compounds, and most preferably no detectable nonyl substituted aryl phosphite compounds. In addition, the phosphite composition preferably comprises less than 50 wppm, e.g., less than 10 wppm, or less than 5 wppm, nonylphenol. Most preferably, the phosphite composition comprises no detectable nonylphenol.

In one embodiment, $R_3$, $R_4$, and $R_5$ are independently selected alkylated aryl groups of the structure of formula (VI):

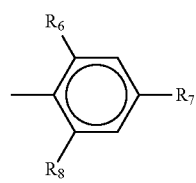

(VI)

wherein $R_6$, $R_7$, and $R_8$ are independently selected from the group consisting of hydrogen and straight or branched $C_1$-$C_8$ alkyl, e.g., methyl, ethyl, propyl, butyl, amyl, hexyl, heptyl, octyl, and isomers thereof, e.g., isopropyl, sec-butyl, tert-butyl, tert-amyl, sec-amyl etc, provided that at least one of $R_6$, $R_7$, and $R_8$ is not hydrogen.

In one embodiment, $R_6$ and $R_7$ are independently selected from the group consisting of methyl, ethyl, propyl, butyl, amyl, hexyl, and isomers thereof, and $R_8$ is hydrogen. In another embodiment, $R_6$ and $R_8$ are hydrogen and $R_7$ is independently selected from the group consisting of methyl, ethyl, propyl, butyl, amyl, hexyl, and isomers thereof. In one aspect of these embodiments, at least one of $R_6$, $R_7$, and $R_8$ are $C_4$ or $C_5$ alkyl, often, tert-butyl or tert-amyl.

In one embodiment, $R_3$, $R_4$, and $R_5$ are independently selected alkylated aryl groups of the structure of formula (VII):

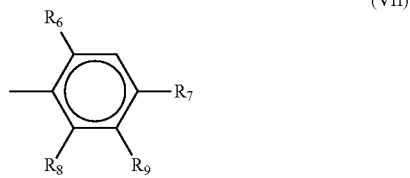

(VII)

wherein $R_6$, $R_7$, and $R_8$ are defined above and $R_9$ is hydrogen or methyl, provided that one of $R_6$, $R_7$, $R_8$, and $R_9$ is methyl and that at least two of $R_6$, $R_7$, $R_8$, and $R_9$ are not hydrogen. Such phosphites may be formed, for example, by the reaction of one or more alkylated cresol compounds, e.g., one or more of alkylated ortho-, meta-, and/or para-cresol, with $PCl_3$.

In some preferred embodiments, the liquid phosphite composition comprises at least two phosphites selected from the group consisting of tris(4-t-butylphenyl)phosphite, tris(2-t-butylphenyl)phosphite, tris(2,4-di-t-butylphenyl)phosphite, bis(4-t-butylphenyl)-2,4-di-t-butylphenyl phosphite, bis(2,4-di-t-butylphenyl)-4-t-butylphenyl phosphite, bis(2-t-butylphenyl)-2,4-di-t-butylphenyl phosphite, bis(2,4-di-t-butylphenyl)-2-t-butylphenyl phosphite, tris(4-t-amylphenyl)phosphite, tris(2-t-amylphenyl)phosphite, tris(2,4-di-t-amylphenyl)phosphite, bis(4-t-amylphenyl)-2,4-di-t-amylphenyl phosphite, bis(2,4-di-t-amylphenyl)-4-tamylphenyl phosphite, bis(2-t-amylphenyl)-2,4-di-t-amylphenyl phosphite, and bis(2,4-di-t-amylphenyl)-2-tamylphenyl phosphite. In one embodiment, the phosphite composition does not comprise only phosphites that, when combined in a composition, would result in a solid composition. An example of a phosphite that would result in a solid composition is one produced from the reaction of 2,4-di-t-butylphenol and 2,4-di-t-amylphenol with phosphorus trichloride as described in U.S. Pat. No. 5,254,709.

In many embodiments, the phosphite composition has an overall phosphorus content that is equal to or greater than that of TNPP, e.g., at least 4.5 mole %, e.g., at least 4.8 mole %, or at least 5.1 mole %. In terms of ranges, the overall phosphorus content of the phosphite composition may range, from 4.5 to 10.0 mole %, e.g., from 4.8 to 8.0 mole %, or 5.1 to 6.0 mole %, based on the total moles of all phosphorous-containing compounds in the phosphite composition.

As indicated above, the phosphite composition often comprises at least two of the following: a tris(dialkylaryl)monophosphite, a tris(monoalkylaryl)phosphite, a bis(dialkylaryl)monoalkylaryl phosphite, and a bis(monoalkylaryl)dialkylaryl phosphite, wherein the phosphite composition is a liquid at ambient conditions. The relative amounts of the respective phosphite components contained in the phosphite composition may vary somewhat so long as the phosphite composition itself is a liquid at ambient conditions. In these embodiments the phosphite composition comprises at least two of these compounds, at least three of these compounds, or all four of these compounds, in an amount greater than 80 wt. %, 90 wt. %, or 95 wt. %, based on the total weight of all phosphite compounds in the phosphite composition. Of course, a minor amount of other species, phosphite or non-phosphite, may be present in these compositions, e.g., one or more of tris(2-tert-amylphenyl)phosphite, bis(2-tert-amylphenyl)-2,4-di-tert-amylphenyl phosphite, bis(2,4-di-tert-amylphenyl)-2-tert-amylphenyl phosphite, and the like.

The relative amounts of the respective phosphite components contained in the liquid phosphite composition may vary somewhat so long as the phosphite composition is a liquid at ambient conditions. For example, one particular phosphite composition comprises a tris(monoalkylaryl)phosphite, e.g., tris(4-t-amyl-phenyl)phosphite, in an amount from 20 to 70 wt. %, e.g., from 15 to 55 wt. %, or from 37 to 54 wt. %, and a bis(monoalkylaryl)dialkylaryl phosphite, e.g., bis(4-t-amyl-phenyl)-2,4-di-t-amyl-phenyl)phosphite, in an amount from 15 to 60 wt. %, e.g., from 31 to 50 wt. %, or from 34 to 45 wt. %. Optionally, the phosphite composition further comprises a tris(dialkylaryl)phosphite, and/or bis(dialkylaryl)monoaryl phosphite. If present, the tris(dialkylaryl)phosphite, e.g., tris(2,4-di-tert-amyl-phenyl)phosphite, preferably is present in an amount of from 0.1 to 20 wt. %, e.g., from 0.3 to 5 wt. %, or from 0.5 to 1 wt. %. If present, the bis(dialkylaryl)monoaryl phosphite, e.g., bis(2,4-di-tert-amyl-phenyl)-4-t-amyl-phenyl phosphite, preferably is present in an amount of from 2 to 20 wt. %, e.g., from 4 to 20 wt. %, or from 5 to 10 wt. %. Unless otherwise indicated, weight percent (wt. %) is based on the total weight of the phosphite composition.

In these embodiments, the phosphite composition often has a weight ratio of tris(monoalkylaryl)phosphites to the combination of bis(monoalkylaryl)dialkylaryl phosphites, bis(dialkylaryl)monoalkylaryl phosphites and tris(dialkylaryl)phosphites of from 1:4 to 7:3, e.g., from 2:5 to 3:2, or from 3:5 to 6:5. The phosphite composition optionally has a weight ratio of bis(monoalkylaryl)dialkylaryl phosphites to the combination of tris(monoalkylaryl)phosphites, bis(dialkylaryl)monoalkylaryl phosphites and tris(dialkylaryl)phosphites of from 1:6 to 3:2 e.g., from 1:3 to 1:1, or from 1:2 to 2:3. The phosphite composition optionally has a weight ratio of bis(dialkylaryl)monoalkylaryl phosphites to the combination of tris(monoalkylaryl)phosphites, bis(monoalkylaryl)dialkylaryl phosphites, and tris(dialkylaryl)phosphites of from 1:50 to 2:5, e.g., from 1:30 to 1:5, or from 1:20 to 1:9, or optionally less than 0.2:1, less than 0.1:1, less than 0.05:1, or less than 0.02:1.

Often, the liquid phosphite composition comprises at least two of a tris(di-$C_3$-$C_5$ alkylaryl)phosphite, a tris($C_3$-$C_5$ alkylaryl)phosphite, a bis(di-$C_3$-$C_5$ alkylaryl)$C_3$-$C_5$ alkylaryl phosphite, and a bis($C_3$-$C_5$ alkylaryl)di-$C_3$-$C_5$ alkylaryl phosphite. Preferably the composition comprises each of the these phosphites in the following amounts: 1-5 wt % of the tris(di-$C_3$-$C_5$ alkylaryl)phosphite, 10-70 wt % of the tris($C_3$-$C_5$ alkylaryl)phosphite, 1-35 wt % of the bis(di-$C_3$-$C_5$ alkylaryl)$C_3$-$C_5$ alkylaryl phosphite, and 5-70 wt % of the bis($C_3$-$C_5$ alkylaryl)di-$C_3$-$C_5$ alkylaryl phosphite.

Liquid phosphite mixtures may be characterized based on how the aryl moieties, e.g., phenyl moieties, are substituted, e.g., alkyl (e.g., t-butyl or t-amyl) substituted, as a whole. For example, in one embodiment, a majority of the aryl moieties are mono substituted in the para-position, e.g., at least 50%, at least 70%, or at least 90% mono substituted in the para-position, optionally from 50 to 95%, e.g., from 55 to 90, or from 60 to 85% mono substituted in the para-position, based on the number of aryl moieties in the phosphite composition. In other embodiments, some of the aryl moieties are disubstituted, e.g., ortho- and para-disubstituted, at least in part, for example, least 10% of the aryl moieties are ortho- and para-disubstituted, e.g., at least 20% ortho- and para-disubstituted, or at least 50% ortho- and para-disubstituted, optionally from 5 to 50% ortho- and para-disubstituted, e.g., from 10 to 45% ortho- and para-disubstituted, or from 15 to 40% ortho- and para-disubstituted, based on the total number of aryl moieties in the phosphite composition. In other embodiments, the ratio of monoalkylaryl groups to dialkylaryl groups ranges from 5:1 to 1:1, e.g., from 4:1 to 1:1, or from 3.5:1 to 2:1.

In many embodiments wherein the liquid phosphite compositions include phosphite compounds having aryl moieties that are monoalkylated and dialkylated, few if any of the aryl moieties are trisubstituted. For example, fewer than 3 wt. % of the aryl moieties are trisubstituted, e.g., fewer than 2 wt. %, or fewer than 1 wt. %. Similarly, in these mixtures, few if any of the aryl moieties are monosubstituted in the ortho position. Preferably, the aryl moieties are monosubstituted in the ortho position, if at all, in an amount less than 3 wt. %, e.g., less than 2 wt. %, or less than 1 wt. %.

Other Stabilizers

As discussed above, a stabilizing amount or effective amount of the hydrolytically stabilized phosphite composition of the invention may be used as a secondary antioxidant for various types of polymers. As used herein, by "stabilizing amount" and an "effective amount" it is meant when the polymer composition containing the hydrolytically stabilized phosphite compositions of the invention shows improved stability in any of its physical or color properties in comparison to an analogous polymer composition which does not include a hydrolytically stabilized phosphite composition. Examples of improved stability include improved stabilization against, for example, molecular weight degradation, color degradation, and the like from, for example, melt processing, weathering, and/or long term field exposure to air heat, light, and/or other elements. In one example, improved stability is obtained in the form of one or both of lower initial color as measured by yellowing index and melt flow rate of the molten polymer or additional resistance to weathering, as measured, for example, by initial yellowness index (YI), or by resistance to yellowing and change in color, when compared to a composition without the stabilizer additive.

The additives and stabilizers described herein are preferably present in an amount effective to improve composition stability. When one of the aforementioned hydrolytically stabilized phosphite compositions is utilized, the composition is generally present in an amount from about 0.001 to about 5 wt. %, e.g., from about 0.0025 to about 2 wt. %, or from about 0.005 to about 1 wt. %, based on the total weight of the polymer including the weight of the phosphite composition, amines, and any other stabilizers or additives. The hydrolytically stabilized phosphite compositions of this invention stabilize resins especially during high temperature processing with relatively little change in melt index and/or color, even after multiple extrusions.

The invention further relates to a stabilized thermoplastics, comprising a base polymer (e.g., polymer resin) and any of the aforementioned hydrolytically stabilized phosphite compositions of the invention. The polymer may be a polyolefin, and phosphite may be a liquid phosphite composition in combination with a co-stabilizer, for example, hindered phenolics, aromatic amines, hydroxylamines, lactones, and thioethers. Thus, the thermoplastic that is stabilized by the hydrolytically stabilized phosphites of the present invention may optionally contain one or more additional stabilizers or mixtures of stabilizers selected from the group consisting of the phenolic antioxidants, hindered amine light stabilizers (HALS), the ultraviolet light absorbers, phosphites, phosphonites, alkaline metal salts of fatty acids, hydrotalcites, metal oxides, epoxydized soybean oils, the hydroxylamines, the tertiary amine oxides, lactones, thermal reaction products of tertiary amine oxides, and the thiosynergists.

In one embodiment, the amount of each component in the stabilizing mixture, based on the total weight percent of the polymer or polymeric resin, is shown in Table 3.

TABLE 3

| Component | Range | Preferred Range |
|---|---|---|
| Liquid phosphite compositions | 0.001-5.0 wt % | 0.005-1.0 wt % |
| Primary antioxidant | 0-5.0 wt % | 0.005-2.0 wt % |
| UV or light stabilizers | 0-3.0 wt % | 0.001-2.0 wt % |
| Metal deactivators | 0-3.0 wt % | 0.001-2.0 wt % |
| Other secondary antioxidants | 0-3.0 wt % | 0.001-2.0 wt % |
| Peroxide scavengers | 0-3.0 wt % | 0.001-2.0 wt % |
| Polyamide stabilizers | 0-3.0 wt % | 0.001-2.0 wt % |
| Basic co-stabilizers | 0-3.0 wt % | 0.001-2.0 wt % |
| Nucleating or clarifying agents | 0-3.0 wt % | 0.001-2.0 wt % |
| Aminoxy propanoate | 0-3.0 wt % | 0.001-2.0 wt % |

Primary antioxidants include the following:

(i) Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2,6-bis(α-methylbenzyl)-4-methylphenol, 2-(α-methylcyclohexyl)-4,6-dimethylphenol, 2,6-dioctadecyl-4-methylphenol, 2,4,6,-tricyclohexylphenol, and 2,6-di-tert-butyl-4-methoxymethylphenol. Commercially available alkylated monophenols include Lowinox™ 624 and Naugard™ 431. Other phenols are commercially available such as BHEB.

(ii) Alkylated hydroquinones, for example, 2,6-di-tert-butyl-4-methoxyphenol, 2,5-di-tert-butyl-hydroquinone, 2,5-di-tert-amyl-hydroquinone, and 2,6-diphenyl-4octadecyloxyphenol. Commercially available alkylated hydroquinones include Lowinox AH25 made by Chemtura.

(iii) Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), and 4,4'-thio-bis-(6-tert-butyl-2-methylphenol). Commercially available hydroxylated thiodiphenyl ethers include Lowinox TBM6, and Lowinox TBP6.

(iv) Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(α-methylbenzyl)-4-nonylphenol), 2,2'-methylene-bis-(6-(alpha,alpha-dimethylbenzyl)-4-nonyl-phenol), 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 1,1-bis(2-methyl-4-hydroxy-5-tert-butylphenyl)butane, 2,2'-isobutylidene-bis(4,6-dimethylphenol), 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, and di-(2-(3'-tert-butyl-2'hydroxy-5'methyl-benzyl)-6-tert-butyl-4-methylphenyl)terephthalate. Commercially available alkylidene-bisphenols include Lowinox 22M46, Lowinox WSP, Lowinox 44B25, Naugard 536, Naugawhite™, and Lowinox 221B46.

(v) Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate, 1,3,5- tris-(3,5-di-tert-butyl-4 hydroxybenzyl)isocyanurate, 1,3,5-tris-(4-tert-butyl-3-hydroxy-2,6-dimethylbenzyl) isocyanurate, 1,3,5-tris(4-t-butyl-3-hydroxy-2,6-dimethylbenzyl)-1,3,5-Triazine-2,4,6-(1H,3H,5H)-trione, dioctadecyl-3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl)isocyanurate. Commercially available benzyl compounds include Anox™ IC-14, Anox 330 and Lowinox 1790.

(vi) Acylaminophenols, for example, 4-hydroxylauric acid anilide, 4-hydroxy-stearic acid amilide, 2,4-bis-octylmercapto-6-(3,5-tert-butyl-4-hydroxyanilino) -s-triazine, and octyl-N-(3,5-di-tert-butyl-4-hydroxyphenyl)-carbamate.

(vii) Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl oxalic acid diamide. Such phenols also include tetrakis [methylene {3,5-di-tert-butyl-4-hydroxycinnamate}]methane. Commercially available esters include Anox 20, Anox 1315, Lowinox GP45, Naugalube 38, Naugalube 531, Anox PP18, Naugard PS48 and Naugard XL-1.

(viii) Thio esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide. Commercially available thio esters include Naugalube™ 15 and Anox 70.

(ix) Amides of beta-(3,5-di-tert-butyl-4-hydroxyphenol)-propionic acid for example, N,N'-di-(3,5-di-tert-butyl-4-hydroxyphenylpropionyl)-hexammethylen-diamine, N,N'-di-(3,5-di-tert-butyl-4-hydroxyphenylpropionyl) trimethylenediamine, N,N'-di-(3,5-di-tert-butyl-4-hydroxyphenylpropionyl)-hydrazine, N,N'-Hexamethylene bis[3-(3,5-di-t-butyl-4-hydroxyphenyl)propionamide, and 1,2-Bis(3,5-di-tert-butyl-4-hydroxyhydrocinnamoyl)hydrazine. Commercially available amides include Lowinox HD98 and Lowinox MD24.

(x) Other phenolic antioxidants include the following phenols. Polymeric phenols such as the reaction product of 4-methylphenol with dicyclopentadiene and isobutylene, commercially available as Lowinox CP. Alkylidene-poly-phenols, such as 1,3 tris(3-methyl-4-hydroxyl-5-t-butyl-phenyl)-butane (Lowinox CA22). Thio phenols such as 2,6-di-tert-butyl-4-(4,6-bis(octylthio)-1,3,5-triazin-2-ylamino)phenol (Irganox™ 565), 4,6-bis(octylthiomethyl)-o-cresol (Irganox 1520); 4,6-bis(dodecylthiomethyl)-o-cresol (Irganox 1726). Hydroxyl amines, such as bis(octadecyl)hydroxylamine (Irgastab™ FS 042). Ester phenols include bis[3,3-bis(4-hydroxy-3-tert-butyl phenyl)butanoic acid]glycol ester (Hostanox™ O3). Still other phenols include 2-[1-(2-hydroxy-3, 5-di-tert-pentylphenyl)ethyl]-4,6-di-tert-pentylphenyl acrylate (Sumilizer GS). In one embodiment, the stabilizing composition comprises one phenolic selected from the group of tetrakismethylene(3,5-di-t-butyl-4-hydroxylhydrocinnamate)methane (Anox 20), 1,3,5-tris(3,5-di-t-butyl-4-hydroxybenzyl)isocyanurate (Anox IC-14), 1,3,5-tris(4-tert.-butyl-3-hydroxy-2,6-dimethylbenzyl)-1,3,5-triazine-2,4,6-(1H,3H,5H)-trione (Lowinox 1790), octyl-3-(3,5-di-t-butyl-4-hydroxyphenyl)propionate (Anox PP18), bis(octadecyl) hydroxylamine (Irgastab FS-042), 1,3,5-trimethyl-2,4,6-tris (3,5-di-tert-4-hydroxybenzyl)benzene (Anox 330), 2,6-bis (α-methylbenzyl)-4-methylphenol (Naugalube 431), 3,5-bis (1,1-dimethylethyl)-4-hydroxy-benzenepropanoic acid (Anox 1315), 2,6-di-t-butyl-4-ethyl-phenol (BHEB), and mixtures thereof, and the liquid phosphite composition defined herein.

The hydrolytically stabilized phosphites and/or the resulting stabilized polymeric resin compositions optionally also comprise one or more UV absorbers and/or light stabilizers, such as the following:

(i) 2-(2'-hydroxyphenyl)-benzotriazoles, for example, the 5'-methyl-, 3'5'-di-tert-butyl-,3,5'-di-tert-amyl-, 5'-tert-butyl-, 5'-tert-amyl-, 5'(1,1,3,3-tetramethylbutyl)-, 5-chloro-3', 5'-di-tert-butyl-, 5-chloro-3'-tert-butyl-5'-methyl-, 3'-sec-butyl-5'-tert-butyl-,4'-octoxy, 3',5'-ditert-amyl-3',5'-bis-(α,α-dimethylbenzyl)-derivatives. Commercially available 2-(2'-hydroxyphenyl)-benzotriazoles include Lowilite™ 26, Lowilite 27, Lowilite 28, Lowilite 29, Lowilite 35, Lowilite 55, and Lowilite 234.

(ii) 2-Hydroxy-benzophenones, for example, the 4-hydroxy, 4-methoxy-, 4-octoxy, 4-decyloxy-, 4-dodecyloxy-, 4-benzyloxy-, 2,4-dihydroxy-, 4,2',4'-trihydroxy- and 2'-hydroxy-4,4'-dimethoxy-derivative. Exemplary 2-hydroxy-benzophenones include 2-hydroxy-4-methoxybenzophenone, 2-hydroxy-4-ethoxybenzophenone, 2,4-dihydroxybenzophenone, and 2-hydroxy-4-propoxybenzophenone. Commercially available 2-(2'-hydroxyphenyl) -benzotriazoles include Lowilite 20, Lowilite 22, Lowilite 20S, and Lowilite 24.

(iii) Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butylphenyl-3,5-di-tert-butyl-4-hydroxybenzoate and hexadecyl-3,5-di-tert-butyl-4-hydroxybenzoate.

(iv) UV absorbers and light stabilizers may also comprise acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

(v) Nickel compounds are also suitable UV absorbers and light stabilizers. Exemplary nickel compounds include nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands. Commercially available nickel compounds include Lowilite Q84 (2,2'-Thiobis(4-tert-octyl-phenolato))-N-butylamine-Nichel(II).

(vi) Sterically hindered amines may be used as UV absorbers and light stabilizers. Sterically hindered amines, for example bis(2,2,6,6-tetramethylpiperidyl)-sebacate, bis-(1, 2,2,6,6-pentamethylpiperidyl)-sebacate, n-butyl-3,5-di-tert-butyl-4-hydroxybenzyl malonic acid bis(1,2,2,6,6-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octy-lamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2- ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperidine; and N-(1-hydroxy-2,2,6,6-tetramethyl-piperidin-4-yl)-epsiloncaprolactam. Commercially available hindered amines include Lowilite 19, Lowilite 62, Lowilite 77, Lowilite 92 and Lowilite 94.

(vii) Oxalic acid diamides, for examples, 4,4'-dioctyloxy-oxanilide, 2,2'-di-octyloxy-5',5'-di-tert-butyloxanilide, 2,2'-di-dodecyloxy-5',5'di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of o- and p-methoxy—as well as of o- and p-ethoxy-disubstituted oxanilides.

The polymer resins and phosphite compositions of the invention may also include one or more additional additives, including, for example, one or more of the following:

(i) Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

(ii) Additional secondary antioxidants such as additional phosphites and/or phosphonites, for example, triphenyl phosphite, diphenylalkyl phosphites, phenyldialkyl phosphites, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, bis(2,4-di-cumylphenyl)pentaerythritol diphosphite, and tetrakis(2,4-di-tert-butylphenyl)4,4'-biphenylene diphosphonite. Commercially available secondary antioxidants include Naugalube TPP, Alkanox™ 240, Ultranox™ 626, Naugard P, Weston™ 399, Weston TNPP, Weston 430, Weston 618F, Weston 619F, Weston DPDP, Weston DPP, Weston PDDP, Weston PTP, Weston TDP, Weston TLP, Weston TPP, and Weston TLTTP (trilauryl trithio phosphite); Doverphos™ 4, Doverphos 4-HR, Doverphos 4-HR Plus, Doverphos HiPure 4, and Doverphos S-9228; and Hostanox PEPQ.

(iii) Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

(iv) Polyamide stabilizers, for example copper salts in combination with iodides and/or phosphorus compounds and salts of divalent manganese may also be included in the polymer resin and/or phosphite composition.

(v) Basic co-stabilizers, for example, melamine, polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate. Commercially available co-stabilizers include Mark™ 6045, Mark 6045ACM, Mark 6055, Mark 6055ACM, Mark 6087ACM, Mark 6102, Mark CE 345, Mark CE 350, and Mark CE 387; and DHT-4A™.

(vi) Nucleating and clarifying agents, for example, metal salts of 4-tert butylbenzoic acid, adipic acid, diphenylacetic acid, sorbitol and derivatives thereof, sodium benzoate, and benzoic acid.

(vii) Aminoxy propanoate derivatives such as methyl-3-(N,N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

(viii) Other additives, for example, plasticizers, lubricants, emulsifiers, pigments, optical brighteners, flameproofing agents, anti-static agents, blowing agents and thiosynergists such as dilaurythiodipropionate or distearylthiodipropionate.

Optionally the polymer or polymeric resins may include from 5-50 wt %, e.g., 10-40 wt % or 15-30 wt % fillers and reinforcing agents, for example, calcium carbonate, silicates, glass fibers, asbestos, talc, kaolin, mica, barium sulfate, metal oxides and hydroxides, carbon black and graphite.

Polymers

The invention further pertains to a stabilized polymer, wherein one component comprises a liquid phosphite composition, as described herein, and the other a polymer, such as a polyolefin, polyvinyl chloride, etc., or polymeric resins.

The polymer stabilized by such liquid phosphite compositions may be any polymer known in the art, such as polyolefin homopolymers and copolymers, thermoplastics, rubbers, polyesters, polyurethanes, polyalkylene terephthalates, polysulfones, polyimides, polyphenylene ethers, styrenic polymers and copolymers, polycarbonates, acrylic polymers, polyamides, polyacetals, halide-containing polymers, and biodegradable polymers. Mixtures of different polymers, such as polyphenylene ether/styrenic resin blends, polyvinyl chloride/ABS or other impact modified polymers, such as methacrylonitrile and α-methylstyrene containing ABS, and polyester/ABS or polycarbonate/ABS and polyester plus some other impact modifier may also be used. Such polymers are available commercially or may be made by means well known in the art. However, the stabilizer compositions of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

The polymers used in combination with liquid phosphite compositions, as described herein, are produced using a variety of polymerization processes including solution, high-pressure, slurry and gas phase using various catalysts including Ziegler-Natta, single-site, metallocene or Phillips-type catalysts. Non-limiting polymers useful with the liquid phosphite compositions include ethylene based polymers such as linear low density polyethylene, elastomers, plastomers, high density polyethylene, substantially linear long chain branched polymers, and low density polyethylene; and propylene based polymers such as polypropylene polymers including atactic, isotactic, and syndiotactic polypropylene polymers, and propylene copolymers such as propylene random, block or impact copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. The polymers produced by the process of the invention typically have a molecular weight distribution, a weight average molecular weight to number average molecular weight (Mw/Mn) of greater than 1.5 to about 15, particularly greater than 2 to about 10, more preferably greater than about 2.2 to less than about 8, even more preferably from about 2.2 to less than 5, and most preferably from 2.5 to 4. The ratio of Mw/Mn can be measured by gel permeation chromatography techniques well known in the art. The polymers of the present invention in one embodiment have a melt index (MI) or (I2) as measured by ASTM-D-1238-E in the range from 0.01 dg/min to 1000 dg/min, more preferably from about 0.01 dg/min to about 100 dg/min, even more preferably from about 0.1 dg/min to about 50 dg/min, and most preferably from about 0.1 dg/min to about 10 dg/min. The polymers of the invention in one embodiment have a melt index ratio (I21/I2) (I21 is measured by ASTM-D-1238-F) of from 10 to less than 25, more preferably from about 15 to less than 25. The polymers of the invention in a preferred embodiment have a melt index ratio (I21/I2) (I21 is measured by ASTM-D-1238-F) of from preferably greater than 25, more preferably greater than 30, even more preferably greater that 40, still even more preferably greater than 50 and most preferably greater than 65.

Polymers used with liquid phosphites compositions of the invention are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc. In addition to the above, the liquid phosphite compositions are used in various rubber based products such as tires, barriers and the like.

In one embodiment, the liquid phosphite compositions are suitable and/or approved for use in polymers, preferably polyolefins, that are used in contact with beverages, foods and other human consumables.

Polymers of monoolefins and diolefins, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA, and LLDPE/EAA.

The olefin polymers may be produced by, for example, polymerization of olefins in the presence of Ziegler-Natta catalysts optionally on supports such as, for example, MgCl2, chromium 20 salts and complexes thereof, silica, silica-alumina and the like. The olefin polymers may also be produced utilizing chromium catalysts or single site catalysts, e.g., metallocene catalysts such as, for example, cyclopentadiene complexes of metals such as Ti and Zr. As one skilled in the art would readily appreciate, the polyethylene polymers used herein, e.g., LLDPE, can contain various comonomers such as, for example, 1-butene, 1-hexene and 1-octene comonomers.

The polymer may also include styrenic polymers, such as polystyrene, poly-(p-methylstyrene), 5 poly-(α-methylstyrene), copolymers of styrene or α-methylstyrene with dienes or acrylic derivatives, such as, for example, styrene/butadiene (SBR), styrene/acrylonitrile, styrene/alkyl methacrylate, styrene/maleic anhydride, styrene/maleimide, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene (SBS), styrene/isoprene/styrene (SIS), styrene/ethylene/butylene/styrene or styrene/ethylene/propylene/styrene.

Styrenic polymers may additionally or alternatively include graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Suitable rubbers include both natural rubber and synthetic rubbers, and combinations thereof. Synthetic rubbers include, but are not limited to, for example, thermoplastic rubbers, ethylene/alpha-olefin/non-conjugated polyene (EPDM) rubbers, ethylene/alpha-olefin (EPR) rubbers, styrene/butadiene rubbers, acrylic rubbers, nitrile rubbers, polyisoprene, polybutadiene, polychloroprene, acrylonitrile/butadiene (NBR) rubbers, polychloroprene rubbers, polybutadiene rubbers, isobutylene-isoprene copolymers, etc. Thermoplastic rubbers include SIS, solution and emulsion SBS, etc.

Nitrile polymers are also useful in the polymer composition of the invention. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be stabilized with the hydrolytically stabilized phosphites. These include polymers such as polychloroprene, epichlorohydrin homo- and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloridestyrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful polymers include homopolymers and copolymers of cyclic ethers, such as polyalkylene glycols, polyethylene oxide, polypropylene oxide or copolymers thereof with bisglycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2-(2,2,4(4-hydroxyphenyl)-propane)terephthalate and polyhydroxybenzoates as well as block copolyetheresters derived from polyethers having' hydroxyl end groups.

Polyamides and copolyamides which are derived from bisamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene bisamine and adipic acid; polyamides prepared from hexamethylene bisamine and isophthalic or/and terephthalic acid and optionally an elastomer as modifier, for example poly-2,4,4 trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

In another embodiment, the polymer comprises a biodegradable polymer or compostable polymer. Biodegradable polymers are those in which the degradation results from the action of naturally occurring microorganisms, such as bacteria, fungi and algae. Compostable polymers undergoes degradation by biological processes during composting to yield $CO_2$, water, inorganic compounds and a biomass at a rate consistent with other compostable materials. Typically the biodegradable or compostable polymers are derived from plant sources and are synthetically produced. Examples of biodegradable or compostable polymers include poly(glycolic acid) (PGA), poly(lactic acid) (PLA), and co-polymers thereof. Biodegradable or compostable polymers may also be derived from a blend of starch of a plant and a conventional petroleum-based polymer. For example, the biodegradable polymer may be blended with a polyolefin.

Polyolefin, polyalkylene terephthalate, polyphenylene ether and styrenic polymers, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

In one embodiment, the liquid phosphite compositions are added to stabilize natural and synthetic waxes, such as n-paraffin waxes, chloroparaffins, $\alpha$-olefin waxes, microcrystalline waxes, polyethylene waxes, amide waxes, and Fisher-Tropsch waxes. These waxes may be suitable for making candles.

The instant stabilizers may readily be incorporated into the polymer by conventional techniques at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized compositions of the invention may optionally also contain from about 0.001 to about 5 wt. %, e.g., from about 0.0025 to about 2 wt. % or from about 0.05 to about 0.25 wt. %, of various conventional additives, such as those described previously, or mixtures thereof.

The stabilizers of this invention advantageously assist with the stabilization of polymer compositions especially in high temperature processing against changes in melt index and/or color, even though the polymer may undergo a number of extrusions. The stabilizers of the present invention may readily be incorporated into the polymer compositions by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer.

The compositions of the present invention can be prepared by a variety of methods, such as those involving intimate admixing of the ingredients with any additional materials desired in the formulation. Suitable procedures include solution blending and melt blending. Because of the availability of melt blending equipment in commercial polymer processing facilities, melt processing procedures are generally preferred. Examples of equipment used in such melt compounding methods include: co-rotating and counter-rotating extruders, single screw extruders, disc-pack processors and various other types of extrusion equipment. In some instances, the compounded material exits the extruder through small exit holes in a die and the resulting strands of molten resin are cooled by passing the strands through a water bath. The cooled strands can be chopped into small pellets for packaging and further handling.

All of the ingredients may be added initially to the processing system, or else certain additives may be pre-compounded with each other or with a portion of the polymer or polymeric resin to make a stabilizer concentrate. Moreover, it is also sometimes advantageous to employ at least one vent port to allow venting (either atmospheric or vacuum) of the melt. Those of ordinary skill in the art will be able to adjust blending times and temperatures, as well as component addition location and sequence, without undue additional experimentation.

While the stabilizers of this invention may be conveniently incorporated by conventional techniques into polymers before the fabrication thereof into shaped articles, it is also possible to apply the instant stabilizers by a topical application to the finished articles. Articles may comprise the instant stabilizer compounds and polymers and may be made into, for example, head lamp covers, roofing sheets, telephone covers, aircraft interiors, building interiors, computer and business machine housings, automotive parts, and home appliances. The articles may be made by extrusion, injection molding, roto-molding, compaction, and other methods. This may be particularly useful with fiber applications where the instant stabilizers are applied topically to the fibers, for example, by way of a spin finish during the melt spinning process. In one embodiment, the liquid phosphite compositions should be approved for use in polymeric resins, preferably polyolefins, that are used in contact with beverages, foods and other human consumables.

The hydrolytically stabilized phosphite composition of the invention may have uses in addition to polymer stabilization. For example, it may be desirable to react the phosphite composition to form a new derivative product, that may have additional uses. Transesterification processes, for example, such as those disclosed in Hechenbleikner et al., U.S. Pat. No. 3,056,823, which is incorporated herein by reference, may also be employed. Specifically, the process described by Hechenbleikner et al. involves transesterifying a triaryl phosphite with a monohydroxy hydrocarbon in the presence of a small but catalytically effective amount of a metal alcoholate or metal phenolate. To avoid contamination, the alcoholate of the particular alcohol to be transesterified is employed. Instead of employing a preformed alcoholate, the alcoholate can be formed in situ by adding the metal, e.g., sodium, potassium or lithium to the alcohol prior to adding the triaryl phosphite. The mono alcohol and triaryl phosphite are reacted in the mol ratio of three mols of the alcohol to one mol of the triaryl phosphite.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

The present invention will now be described by way of the following non-limiting examples.

EXAMPLE 1

Table 4 demonstrates the improved hydrostability of phosphites and liquid phosphite compositions when utilized together with various hydrolysis stabilizers. The hydrolytic stabilizers used in Example 1 included: A=epoxide soybean oil (e.g., Drapex 6.8), B=triisopropanolamine (TIPA), C=Ethoxylated tallowalkylamine (Armostat 300), and D=Octadecylbis(2-hydroxyethyl)amine (Armostat 1800). The liquid phosphite composition analyzed included trinonylphenyl phosphite (TNPP) and a Mono/Di t-amylphenyl phosphite composition (designated Liquid X), which comprised the following phosphites: 30-50 wt % tri(4-t-amylphenyl)phosphite; 30-50 wt % bis(4-t-amylphenyl)(2,4-di-t-amylphenyl)phosphite; 5-15 wt % (4-t-amylphenyl)bis(2,4-di-t-amylphenyl)phosphite; and less than 4 wt % of tri (2,4-di-t-amylphenyl)phosphite.

Approximately 0.025 g samples of the unadditised and additised TNPP and Liquid X were weighed into GC vials, and the vials stored in a humidity chamber at 50° C. and 80% relative humidity. Vials were removed from the chamber on a daily basis and analyzed by 31P {1H} NMR to ascertain when the phosphite had degraded. The test was conducted for a maximum duration of 14 days.

TABLE 4

| Run | Phosphite | Hydrolysis Stabilizer Type | Wt % | Survival Time (Days) |
|---|---|---|---|---|
| 1 | TNPP | — | — | 0.5 |
| 2 | TNPP | A | 5 wt % | 1 |
| 3 | TNPP | B | 0.8 wt % | >14 |
| 4 | TNPP | C | 2 wt % | 4 |
| 5 | TNPP | D | 1 wt % | 4 |
| 6 | Liquid X | — | — | 1 |
| 7 | Liquid X | A | 5 wt % | 2 |
| 8 | Liquid X | B | 0.8 wt % | >14 |
| 9 | Liquid X | C | 2 wt % | 13 |
| 10 | Liquid X | D | 1 wt % | 12 |

As shown in Table 4, for both TNPP and Liquid X, the amine stabilizers of the present invention (Type B-D) yielded significant improvements to the hydrostability of the liquid phosphite compositions. In particular ethoxylated tallowalkylamine and octadecylbis(2-hydroxyethyl)amine demonstrated an increased hydrostability of the liquid phosphite composition (Runs 9 and 10) over that of TNPP (Runs 4 and 5).

EXAMPLE 2

The effect of TIPA and octadecylbis(2-hydroxyethyl) amine (Armostat 1800) on the hydrostability and physical appearance of Liquid X (described above) was investigated.

Approximately 0.025 g samples of Liquid X were combined with either 0.8 wt % TIPA or with 2 wt % Armostat 1800. The samples were weighed in GC vials, and the vials stored in a humidity chamber at 50° C. and 80% relative humidity. Vials of Liquid X combined with 0.8 wt % TIPA and vials of Liquid X combined with 2 wt % Armostat 1800 were removed on a daily basis over 1 week. $^{31}$P {$^{1}$H} NMR showed that Liquid X had not degraded. However, during the course of the study, samples of Liquid X combined with 0.8 wt % TIPA became turbid while the sample of Liquid X combined with 2 wt % Armostat 1800 always remained clear and free of turbidity and, as such, still resembled the starting material.

Thus, Armostat 1800 provides similar hydrolytic stability to TIPA, however, the Armostat 1800 does so without the generation of turbidity.

In an analogous test using TNPP combined with 0.8 wt % TIPA, the samples did not develop turbidity.

EXAMPLE 3

Adapted Static Test 4 ml of the phosphites shown in Table 5, optionally with a 1 wt % of TIPA were added to a 12 ml mixture of water and Bromothymol blue indicator. The resulting mixture was heated to 60° C. Hydrolytic degradation of the phosphite, which results in the production of acid, was detected by the color change of the Bromothymol blue indicator. A target minimum for color flip was 8 hours, and the test was conducted for 100 hours.

TABLE 5

| # | Phosphite | Amine | Hours |
|---|---|---|---|
| 1 | TNPP | — | 0 |
| 2 | Liquid X | — | 2 |
| 3 | TNPP | TIPA | 15 |
| 4 | Liquid X | TIPA | 100 |

Good hydrolytic stability is shown for the combination of Liquid X and TIPA over a combination of TNPP and TIPA. This is clearly surprising and unexpected since TIPA would be expected to have similar performance in both TNPP and Liquid X.

EXAMPLE 4

Adapted Dynamic Test 20 g of the phosphites shown in Table 6, optionally with a 1 wt % of TIPA were added to a 60 ml mixture of water and Phenolphthalein indicator. The resulting mixture was heated to 60° C. under vigorous stirring conditions. Hydrolytic degradation of the phosphite, which results in the production of acid, was detected by the color change of the Phenolphthalein indicator. A target minimum for color fade was 20 minutes, and the test was conducted for 120 hours.

TABLE 6

| # | Phosphite | Amine | Hours |
|---|---|---|---|
| 1 | TNPP | — | 1 |
| 2 | Liquid X | — | 1.5 |
| 3 | TNPP | TIPA | 120 |
| 4 | Liquid X | TIPA | 120 |

Good hydrolytic stability was shown for the combinations of Liquid X and TIPA, and for the combinations of the TNPP and TIPA.

EXAMPLE 5

Cyclohexane Reflux 25 ml mixture of water and Bromothymol blue and 25 ml of cyclohexane were combined and heated to a boil. 0.5 gm of the phosphites shown in Table 7, optionally with 1 wt % of TIPA, were added to the boiling mixture by a syringe. The test was conducted for 120 hours.

TABLE 7

| # | Phosphite | Amine | Hours |
|---|---|---|---|
| 1 | TNPP | — | 120 |
| 2 | Liquid X | — | 13 |
| 3 | TNPP | TIPA | 120 |
| 4 | Liquid X | TIPA | 120 |

As shown in Table 7, the TNPP with or without TIPA survived for the test period of 120 hours. However, the addition of TIPA greatly improved the survival of the Liquid X.

In view of the many changes and modifications that can be made without departing from principles underlying the invention, reference should be made to the appended claims for an understanding of the scope of the protection to be afforded the invention.

What is claimed is:

1. A composition comprising:
   (a) a mixture of phosphites which mixture is a liquid at ambient conditions and consists essentially of
   (i) a tris(monoalkylaryl)phosphite in an amount from 20 to 70 wt %;
   (ii) a bis(monoalkylaryl)dialkylaryl phosphite in an amount from 15 to 60 wt %,
   (iii) a tris(dialkylaryl)phosphite in an amount of from 0.1 to 20 wt %; and
   (iv) a bis(dialkylaryl)monoaryl phosphite in an amount of from 2 to 20 wt % and
   (b) an amine having the structure:

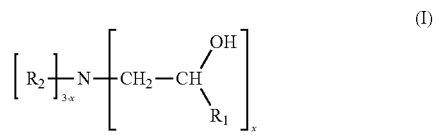

(I)

wherein x is 1, 2 or 3; R1 is selected from the group consisting of hydrogen, and straight or branched C1-C6 alkyl, and R2 is selected from the group consisting of straight or branched C1-C30 alkyl, wherein the phosphites each independently have the structure:

(IV)

wherein $R_3$, $R_4$ and $R_5$ are independently selected alkylated aryl groups of the structure:

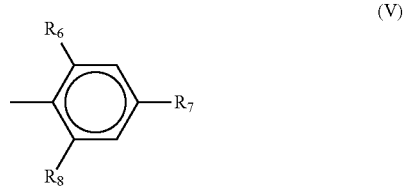

(V)

wherein $R_6$, $R_7$, and $R_8$ are independently selected from the group consisting of hydrogen and straight or branched $C_4$-$C_5$ alkyl, provided that at least one of $R_6$, $R_7$, and $R_8$ is not hydrogen.

2. The composition of claim 1, wherein x is 1 or 2.

3. The composition of claim 1, wherein the amine has the structure

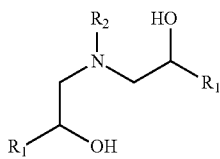

(II)

wherein $R_1$ is hydrogen or methyl; and $R_2$ is a straight or branched $C_8$-$C_{20}$ alkyl group.

4. The composition of claim 1, wherein the amine is selected from the group consisting of octyl-bis(2-ethanol)amine, nonyl-bis(2-ethanol)amine, decyl-bis(2-ethanol)amine, undecyl-bis(2-ethanol)amine, dodecyl-bis(2-ethanol)amine, tridecyl-bis(2-ethanol)amine, tetradecyl-bis(2-ethanol)amine, pentadecyl-bis(2-ethanol)amine, hexadecyl-bis(2-ethanol)amine, heptadecyl-bis(2-ethanol)amine, octadecyl-bis(2-ethanol)amine, octyl- bis(2-propanol)amine, nonyl-bis(2-propanol)amine, decyl-bis(2-propanol)amine, undecyl-bis(2-propanol)amine, dodecyl-bis(2-propanol)amine, tridecyl-bis(2-propanol)amine, tetradecyl-bis(2-propanol)amine, pentadecyl-bis(2-propanol)amine, hexadecyl-bis(2-propanol)amine, heptadecyl-bis(2-propanol)amine, octadecyl-bis(2-propanol)amine, and isomers thereof.

5. The composition of claim 1, wherein the amine has the structure

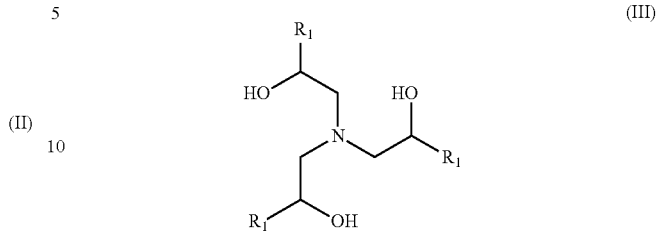

(III)

wherein each $R_1$, is independently selected from the group consisting of hydrogen, straight or branched $C_1$-$C_3$ alkyl.

6. The composition of claim 1, wherein the amine is present in an amount from 0.01 to 3 wt %, based on the total weight of the composition.

7. The composition of claim 1, wherein the phosphites are selected from the group consisting of tris(4-tert-butylphenyl) phosphite, tris(2-tert-butylphenyl) phosphite, tris(2,4-di-tert-butylphenyl) phosphite, bis(4-tert-butylphenyl)-2,4- di-tert-butylphenyl phosphite, bis(2,4-di-tert-butylphenyl)-4-tert-butylphenyl phosphite, bis(2- tert-butylphenyl)-2,4-di-tert-butylphenyl phosphite, bis(2,4-di-tert-butylphenyl)-2-tert-butylphenyl phosphite, tris(4-tert-amylphenyl) phosphite, tris(2-tert -amylphenyl) phosphite, tris(2,4-di-tert-amylphenyl) phosphite, bis(4-tert-amylphenyl)-2,4-di-tert -amylphenyl phosphite, bis(2,4-di-tert-amylphenyl)-4-tertamylphenyl phosphite, bis(2-tert -amylphenyl) -2,4-di-tert-amylphenyl phosphite, and bis(2,4-di-tert-amylphenyl)-2-tertamylphenyl phosphite.

8. A stabilized polymer composition comprising a polymer and the composition of claim 1.

* * * * *